(12) United States Patent
Todoroki et al.

(10) Patent No.: US 9,820,487 B2
(45) Date of Patent: Nov. 21, 2017

(54) ABSCINAZOLE

(71) Applicant: NATIONAL UNIVERSITY CORPORATION SHIZUOKA UNIVERSITY, Shizuoka-shi, Shizuoka (JP)

(72) Inventors: Yasushi Todoroki, Shizuoka (JP); Yuki Kubojiri, Shizuoka (JP)

(73) Assignee: NATIONAL UNIVERSITY OF SHIZUOKA UNIVERSITY (JP)

( * ) Notice: Subject to any disclaimer, the term of this patent is extended or adjusted under 35 U.S.C. 154(b) by 0 days.

(21) Appl. No.: 15/514,096

(22) PCT Filed: Sep. 16, 2015

(86) PCT No.: PCT/JP2015/076336
§ 371 (c)(1),
(2) Date: Mar. 24, 2017

(87) PCT Pub. No.: WO2016/047533
PCT Pub. Date: Mar. 31, 2016

(65) Prior Publication Data
US 2017/0290335 A1  Oct. 12, 2017

(30) Foreign Application Priority Data
Sep. 26, 2014 (JP) ................... 2014-196773

(51) Int. Cl.
*A01N 43/653* (2006.01)
*C07D 249/08* (2006.01)

(52) U.S. Cl.
CPC ......... *A01N 43/653* (2013.01); *C07D 249/08* (2013.01)

(58) Field of Classification Search
None
See application file for complete search history.

(56) References Cited

FOREIGN PATENT DOCUMENTS

| JP | 2013-158294 A | 8/2013 |
|---|---|---|
| JP | 2013-231014 A | 11/2013 |
| WO | WO 2014/095994 A1 | 6/2014 |

OTHER PUBLICATIONS

International Search Report for International Application No. PCT/JP2015/076336 dated Dec. 22, 2015.
Okazaki, M. et al., Abscinazole-E2B, a practical and selective inhibitor of ABA 8'-hydroxylase CYP707A, Bioorganic &Medicinal Chemistry, 2012, vol. 20, Iss. 10, pp. 3162-3172.

*Primary Examiner* — Alicia L Otton
(74) *Attorney, Agent, or Firm* — Ostrolenk Faber LLP (57) ABSTRACT

A compound represented by formula (I) or a salt thereof has an inhibitory action on abscisic acid 8'-hydroxylase CYP707A. The compound or a salt thereof can be used as a plant growth regulator.

(I)

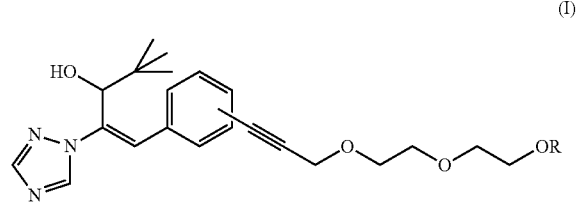

wherein R is a C1-6 alkyl group, and the C1-6 alkyl group optionally have a substituent selected from the group consisting of a halogen atom and a C1-6 alkoxy group.

6 Claims, 4 Drawing Sheets

ABSCINAZOLE

CROSS-REFERENCE TO RELATED APPLICATIONS

The present application is a 35 U.S.C. §§ 371 national phase conversion of PCT/JP2015/076336, filed Sep. 16, 2015, which claims priority to Japanese Patent Application No. 2014-196773, filed Sep. 26, 2014, the contents of both of which are incorporated herein by reference. The PCT International Application was published in the Japanese language.

TECHNICAL FIELD

The present invention relates to an abscinazole.

BACKGROUND ART

Abscisic acid is a phytohormone playing an important role in the seed dormancy and the environmental stress response. The inactivation due to catabolism of abscisic acid is predominantly controlled by abscisic acid 8'-hydroxylase CYP707A.

S-Uniconazole, a plant growth retardant, functions by inhibiting the ent-kaurene oxidase CYP701A enzyme involved in the biosynthesis of gibberellin, but S-uniconazole also inhibits CYP707A. Thus, compounds were developed for removing the CYP701A inhibitory activity from the S-uniconazole function but preserving the CYP707A inhibitory activity and named as abscinazoles. For example, it has been reported that when abscinazole-E2B, one of the abscinazoles, is applied to a plant, the endogenous abscisic acid is not decomposed and that dryness resistance is imparted to the plant (Patent Literature 1 and Non Patent Literature 1).

CITATION LIST

Patent Literature

Patent Literature 1: Japanese Unexamined Patent Publication No. 2013-231014

Non Patent Literature

Non Patent Literature 1: Okazaki et al., "Abscinazole-E2B, a practical and selective inhibitor of ABA 8'-hydroxylase CYP707A", Bioorganic & Medicinal Chemistry, vol. 20, pp. 3162-3172 (2012)

SUMMARY OF INVENTION

Technical Problem

The present invention has an object to provide a novel abscinazole to be an inhibitor of CYP707A.

Solution to Problem

The present inventors have conducted extensive studies and found that a compound formed by replacing the 1,2,3-triazole ring of abscinazole E2B with an acetylenediyl group has a CYP707A inhibitory action, whereby the present invention has been accomplished.

More specifically, the present invention provides a compound represented by formula (I) or a salt thereof:

(I)

[Chemical structure: HO-C(CH3)2-C(=CH-Ar-C≡C-CH2-O-CH2CH2-O-CH2CH2-OR)(1,2,4-triazol-1-yl)]

wherein R is a C1-6 alkyl group, and the C1-6 alkyl group optionally have a substituent selected from the group consisting of a halogen atom and a C1-6 alkoxy group.

In the above compound or a salt thereof, R may be an n-butyl group or a 2-methoxyethyl group.

The compound or a salt thereof can be used as an inhibitor of CYP707A and can also be used as a plant growth regulator.

Advantageous Effects of Invention

The compound represented by formula (I) or a salt thereof has the CYP707A inhibitory action and can be a plant growth regulator.

DESCRIPTION OF EMBODIMENTS

Hereinbelow, the terms herein used will be defined and the present invention will be described in details.

The "halogen atom" herein means a fluorine atom, a chlorine atom, a bromine atom and an iodine atom, with a fluorine atom and a chlorine atom being preferable.

The "C1-6 alkyl group" herein means a straight or branched alkyl group having 1 to 6 carbon atoms, and examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group and an n-hexyl group. The C1-6 alkyl group is, more preferably, a C1-4 alkyl group, which is an alkyl group having 1 to 4 carbon atoms such as a methyl group, an ethyl group, an n-propyl group and an n-butyl group.

The "C1-6 alkoxy group" herein means an oxy group to which a C1-6 alkyl group is bonded, and examples thereof include a methoxy group, an ethoxy group, a 1-propyloxy group, a 2-propyloxy group, a 1-butyloxy group, a 2-methylpropyloxy group, a 1-methylpropyloxy group, a 1,1-dimethylethoxy group.

The compound according to the present embodiment is represented by the formula (I). Hereinafter, the compound is sometimes referred to as the compound (I).

(I)

wherein R is a C1-6 alkyl group, and the C1-6 alkyl group may optionally have a substituent selected from the group consisting of a halogen atom and a C1-6 alkoxy group.

When R is a C1-6 alkyl group with a substituent, the substituent may be at any position and the number of the substituent may be one or more. When the substituent is a C1-6 alkoxy group, the number of the substituent is preferably one.

R is, preferably, a C1-6 alkyl group or a C1-6 alkyl group substituted with a C1-6 alkoxy group.

R is, more preferably, a methyl group, an ethyl group, an n-propyl group, an n-butyl group, a methoxymethyl group, a 2-methoxyethyl group, a 3-methoxypropyl group, a 4-methoxybutyl group, an ethoxy methyl group, a 2-ethoxyethyl group, a 3-ethoxypropyl group or a 4-ethoxybutyl group.

R is, most preferably, an n-butyl group or a 2-methoxyethyl group.

The bonding position of the substituent on the benzene ring of the compound (I) may be any of the ortho position, the meta position and the para position. The meta position and the para position are preferable, and the meta position being most preferable. More specifically, the compound (I) is, preferably, a compound (Ia) or a compound (Ib) shown below, with the compound (Ia) being most preferable. A preferable embodiment of R in the compound (Ia) and the compound (Ib) is the same as the preferable embodiment of R in the compound (I) described above.

(Ia)

(Ib)

The carbon atom at the 3-position in the pent-1-ene chain of the compound (I) is an asymmetric carbon atom, and there are optical isomers of the compound (I). The compound (I) may be the R form, the S form, the racemate or any mixtures of the R form and the S form.

The compound (I) may be in the form of a salt. Examples of the salt include inorganic acid salts and organic acid salts. Examples of the inorganic acid salts include hydrochloride, hydrobromate, sulfate, nitrate and phosphate. Examples of the organic acid salts include acetate, succinate, fumarate, maleate, tartrate, citrate, lactate, stearate, benzoate, methanesulfonate, ethanesulfonate, p-toluenesulfonate and benzenesulfonate.

The compound (I) can be produced by the following reaction scheme:

wherein Ts represents a tosyl group.

Step 1 is reacting 1,2,4-triazole with 1-bromo-3,3-dimethyl-2-butanone in the presence of a base such as potassium carbonate to obtain 3,3-dimethyl-1-(1H-1,2,4-triazol-1-yl)butan-2-one. Examples of the specific reaction condition include those described in Production Example 1.

Step 2 is reacting 3,3-dimethyl-1-(1H-1,2,4-triazol-1-yl)butan-2-one with iodobenzaldehyde to obtain the compound (VI). Examples of the specific reaction condition include those described in Production Examples 2 and 7.

Step 3 is for obtaining the compound (VI-E) from the compound (VI). The E form compound (VI-E) may be separated from the compound (VI), which is a mixture of EZ forms, or the compound (VI), which is a mixture of EZ forms, may be irradiated with a UV light to overincrease the E form compound (VI-E), which is then separated. A typical separation technique such as column chromatography can be used for the separation. Examples of the specific UV irradiation and separation conditions include those described in Production Examples 3 and 8.

Step 4 is by reducing the compound (VI-E) to obtain a compound (V). Using a reducing agent such as sodium borohydride and lithium aluminium hydride, the reaction of Step 4 can be carried out under the reaction conditions commonly employed for the reduction reaction from ketone to alcohol. Examples of the specific reaction conditions include those described in Production Examples 4 and 9.

Step 5 is reacting the compound (V) with the compound (IV) to obtain a compound (II). Examples of the specific reaction condition include those described in Production Examples 6 and 10. The compound (IV) can be produced easily by those skilled in the art using commercial compounds as raw materials. For example, in accordance with the reaction conditions described in Production Example 5, the compound (IV) can be produced.

Step 6 is reacting the compound (II) with a compound (III) to obtain the compound (I). Examples of the specific reaction condition include those described in Examples 1 to 3. The obtained compound (I) may be optically resolved as necessary. The optical resolution can be carried out by a method known by those skilled in art. For example, the optical resolution by chiral HPLC technique can be carried out making reference to Examples 1 to 3 for the conditions.

The (−) form and the (+) form of the compound (I) can be optically resolved to obtain the (−) form, which has higher activity than the (+) form, by the method illustrated in the following reaction scheme alternative to the chiral HPLC technique. According to the following reaction scheme, the expensive chiral column fractionation is obviated and hence the (−) form of the compound (I) can be obtained in a simpler manner at a lower cost.

Step 7 is reacting the compound (I) with N-(p-toluenesulfonyl)-L-phenylalanylchloride to obtain the (−) form of the compound (I) and the compound (VII). When the compound (I) is reacted with N-(p-toluenesulfonyl)-L-phenylalanylchloride in an equivalence ratio of 1:10, most of the (+) forms of the compound (I) react whereas about a half of the (−) forms remains unreacted. The remained, unreacted (−) form of the compound (I) and the compound (VII) can be easily separated by open column chromatography. Thus, the (−) form of the compound (I), which has higher activity, can be obtained by the above method in a simpler manner than the optical resolution using the chiral HPLC. Examples of the specific reaction condition include those described in Example 5.

When the compound (I) is reacted with N-(p-toluenesulfonyl)-L-phenylalanylchloride in an equivalence ratio of 1:20, both of the (−) form and the (+) form of the compound (I) react whereby the compound (VII) is obtained. Step 8 is separating, by HPLC using an ODS column, the compound (VII) into diastereomers and hydrolyzing them using an alkaline aqueous solution such as an aqueous sodium hydroxide solution thereby obtaining the (−) form or the (+) form of the compound (I). Examples of the specific reaction condition include those described in Example 6.

The compound (I) has the CYP707A inhibitory action and hence can suppress the decomposition of abscisic acid by CYP707A. Consequently, when the abscisic acid is synthesized due to stresses, the compound (I)-applied plant maintains the effect of abscisic acid, thereby enabling the enhancement of the abscisic acid effect. Thus, the compound (I) can regulate the plant growth. In particular, it is considered from the action mechanism thereof that stress resistance can be imparted to a plant. For example, even when a plant is exposed to stresses such as dryness, high temperatures or low temperatures, the application of the compound (I) to the plant can prevent the plant from withering.

The target plant is not particularly limited and may be seed plants, pteridophytes or bryophytes. The seed plants may be gymnosperms or angiosperms and the angiosperms may be monocotyledons or dicotyledons.

The target plant organ is not particularly limited and may be any of roots, stems, leaves, flowers, reproductive organs, seeds, and may further be cultured cells.

The concentration and contact method of the compound (I) to be applied to a plant can be suitably adjusted depending on the kind and organ of a target plant and the purpose.

The plant growth regulator containing the compound (I) may contain, in addition to the compound (I), a germicide, an antifungal agent, an insecticide or a compound having the plant growth regulation action other than the compound (I). The regulator may further contain known preparation additives. Examples of the preparation additives include an excipient, an emulsifier and a wetting agent. The form of the plant growth regulator of the present invention is not particularly limited and may be, for examples, an emulsion, a wettable powder, a water soluble powder, a liquid, a granule, a dust, a microcapsule, a fumigant, a smoking agent, an aerosol, a flowable, a paste, a tablet, a coating agent, an agent for ultra-low volume spraying, an oil agent or a compounded fertilizer, from which a user can suitably select in accordance with a target plant and organ thereof and a purpose. The plant growth regulator in these forms can be produced by a known method.

EXAMPLE

Production Example 1

Synthesis of 3,3-dimethyl-1-(1H-1,2,4-triazol-1-yl)butan-2-one

2.06 g (14.9 mmol) of potassium carbonate was dissolved in 5 mL of acetone and 0.98 g (14.0 mmol) of 1,2,4-1H-triazole was added thereto at room temperature. 2 mL (14.9 mmol) of 1-bromo-3,3-dimethyl-2-butanone was added thereto thereby starting the reaction. After stirring at room temperature for 3 hours, the solution was filtered using a filter paper to remove potassium carbonate and the filtrate was concentrated under reduced pressure. The obtained product was subjected to silica gel column chromatography (35 g, 1.5 cm inner diameter×45 cm length) using hexane-acetone (7:3) as an eluent thereby obtaining 1.65 g (9.87 mmol; yield 71%) of the titled compound as a colorless clear needle crystal.

$^1$H-NMR (270 MHz, CDCl$_3$, TMS): δ (ppm) 1.28 (9H, s, t-Bu), 5.20 (2H, s, H-1), 7.96 (1H, s, H-3'), 8.15 (1H, s, H-5')

Production Example 2

Synthesis of 1-(3-iodophenyl)-4,4-dimethyl-2-(1H-1,2,4-triazol-1-yl)pent-1-en-3-one 552.2 mg (2.380 mmol) of 3-iodobenzaldehyde was dissolved in 1 mL of acetic anhydride, and 327.8 mg (2.372 mmol) of potassium carbonate and 405.7 mg (2.426 mmol) of 3,3-dimethyl-1-(1H-1,2,4-triazol-1-yl)butan-2-one were added thereto at room temperature thereby starting the reaction. The solution was stirred for 8 hours at 100° C., 10 hours at room temperature and 12 hours again at 100° C., and subsequently 8 mL of water was added thereto to thereby terminate the reaction. Further 15 mL of water was added thereto, and the resultant was extracted three times with 50 mL of ethyl acetate. The resultant was washed twice with 3 mL of a saturated aqueous solution of sodium chloride, dried over sodium sulfate and subsequently concentrated under reduced pressure thereby obtaining 986.0 mg of a light orange oily substance. The oily substance was subjected to silica gel column chromatography (60 g, 2.4 cm inner diameter×25 cm length) using hexane-acetone (75:25) as an eluent thereby obtaining 551.6 mg (1.447 mmol; yield 61%) of the titled compound as a light yellow oily substance in Z:E=10:3 (calculated from the proton integration ratio at 1-, 3'-, 5'-, 2"-, 4"-, 5"- and 6"-positions of NMR measurement).

Production Example 3

Synthesis of (E)-1-(3-iodophenyl)-4,4-dimethyl-2-(1H-1,2,4-triazol-1-yl)pent-1-en-3-one 123.3 mg of a mixture of the EZ forms of 1-(3-iodophenyl)-4,4-dimethyl-2-(1H-1,2,4-triazol-1-yl)pent-1-en-3-one obtained in Production Example 2 was subjected to silica gel column chromatography (15 g, 1.4 cm inner diameter×16 cm length) using hexane-ethyl acetate (75:25) as an eluent, thereby obtaining 83.4 mg of (Z)-1-(3-iodophenyl)-4,4-dimethyl-2-(1H-1,2,4-triazol-1-yl)pent-1-en-3-one, 16.0 mg of (E)-1-(3-iodophenyl)-4,4-dimethyl-2-(1H-1,2,4-triazol-1-yl)pent-1-en-3-one and 18.1 mg of a mixture of both.

100.1 mg (0.263 mmol) of the mixture of EZ forms obtained in Production Example 2 was dissolved in methanol and the resultant solution was irradiated with a UV lamp (UVP BLACK-RAY LONGWAVE ULTRAVIOLET LAMP, MODEL B-100A) while cooling with ice. The UV irradiation was halted 2 hours later and the resultant solution was concentrated under reduced pressure thereby obtaining 100.2 mg of a light yellow oily substance. The oily substance was subjected to silica gel column chromatography (12 g, 1.2 cm inner diameter×20 cm length) using hexane-ethyl acetate (75:25) as an eluent thereby obtaining 10.3 mg of an EZ mixture and 97.2 mg (0.255 mmol) of the E form as a light yellow oily substance (yield 97%).

Z form
$^1$H-NMR (270 MHz, CDCl$_3$, TMS): δ (ppm) 1.22 (9H, s, t-Bu), 6.68-6.71 (1H, m, H-6"), 6.98 (1H, t, J=7.9 Hz, H-5"), 7.27 (1H, s, H-2"), 7.46 (1H, s, H-1), 7.64-7.68 (1H, m, H-4"), 7.98 (1H, s, H-3'), 8.18 (1H, s, H-5')

E form
$^1$-NMR (270 MHz, CDCl$_3$, TMS): δ (ppm) 1.03 (9H, s, t-Bu), 7.08 (1H, s, H-1) 7.12 (1H, t, J=7.9 Hz, H-5"), 7.30-7.33 (1H, m, H-6"), 7.67-7.70 (1H, m, H-2" and 4"), 8.07 (1H, brs, H-3'), 8.26 (1H, brs, H-5')

high resolution MS: calcd for C$_{15}$H$_{16}$I$_1$N$_3$Na$_1$O$_1$ 404.02357; found 404.02399

Production Example 4

Synthesis of (E)-1-(3-iodophenyl)-4,4-dimethyl-2-(1H-1,2,4-triazol-1-yl)pent-1-en-3-ol

86.8 mg (0.228 mmol) of (E)-1-(3-iodophenyl)-4,4-dimethyl-2-(1H-1,2,4-triazol-1-yl)pent-1-en-3-one was dissolved in 3 mL of methanol, and 11.6 mg (0.307 mmol) of sodium borohydride was added thereto thereby starting the reaction. The solution was stirred at room temperature for 1 hour, subsequently 5 mL of water was added thereby terminating the reaction, and the reaction solution was extracted three times with 15 mL of ethyl acetate. The resultant was washed twice with 1 mL of a saturated aqueous solution of sodium chloride, dried over sodium sulfate and subsequently concentrated under reduced pressure thereby obtaining 88.8 mg of a white solid. The white solid was subjected to silica gel column chromatography (8.5 g, 1.0 cm inner diameter×20.5 cm) using hexane-ethyl acetate (6:4) as an eluent thereby obtaining 86.2 mg (0.225 mmol; yield 99%) of the titled compound as a white solid.
$^1$H-NMR (270 MHz, CDCl$_3$, TMS): δ (ppm) 0.68 (9H, s, t-Bu), 4.26 (1H, d, J=8.6 Hz, OH), 4.53 (1H, d, J=8.6 Hz, H-3), 6.88 (1H, s, H-1), 7.16 (1H, t, J=7.9 Hz, H-5"), 7.34-7.37 (1H, m, H-6"), 7.68-7.76 (2H, m, H-4" and 2"), 8.05 (1H, s, H-3'), 8.48 (1H-1, s, H-5') high resolution MS: calcd for C$_{15}$H$_{18}$I$_1$N$_3$Na$_1$O$_1$ 406.03922; found 406.03914

Production Example 5

Synthesis of 4-methylbenzene sulfonic acid 2-(2-(prop-2-yn-1-yloxy)ethoxy)ethyl

250 μL (4.23 mmol) of propargyl alcohol was dissolved in 30 mL of dehydrated dimethylformamide, and 348 mg (8.7 mmol) of 60% sodium hydride was added thereto and stirred at room temperature for 30 minutes. 3.5 g (8. 5 mmol) of diethylene glycol bis(p-toluene sulfonate) was added thereto while cooling with ice, thereby starting the reaction. After stirring at room temperature for 1 hour, 15 mL of a saturated aqueous solution of ammonium chloride was added thereto thereby terminating the reaction. 60 mL of water was added thereto, 3 mL of 1 M hydrochloric acid was added thereto to adjust pH to be 7, and subsequently the resultant was extracted three times with 100 mL of ethyl acetate. The resultant was washed twice with 3 mL of a saturated aqueous solution of sodium chloride, dried over sodium sulfate and subsequently concentrated under reduced pressure thereby obtaining 3262.5 mg of a mixture of a white solid and a light yellow oily substance. The mixture was subjected to silica gel column chromatography (150 g, 3.0 cm inner diameter× 35 cm length) using hexane-ethyl acetate (75:25) as an eluent thereby obtaining 753.0 mg (2.523 mmol; yield 60%) of the titled compound as a colorless clear oily substance.

Production Example 6

Synthesis of 4-methylbenzene sulfonic acid (E)-2-(2-(3-(3-(3-hydroxy-4,4-dimethyl-2-(1H-1,2,4-triazol-1-yl)pent-1-en-1-yl)phenyl)prop -2-yn-1-yloxy)ethoxy)ethyl 417.9 mg (1.091 mmol) of (E)-1-(3-iodophenyl)-4,4-dimethyl-2-(1H-1,2,4-triazol-1-yl)pent-1-en-3-ol was dissolved in 6 mL of dehydrated tetrahydrofuran under an argon stream, to which 0.76 mL (5.45 mmol) of triethylamine, 19.0 mg (0.0997 mmol) of copper(I) iodide and 20.0 mg (0.0285 mmol) of trans-dichlorobis(triphenylphosphine)palladium (II) were sequentially added. After stirring at room temperature for 30 minutes, 349.0 mg (1.170 mmol) of 4-methylbenzene sulfonic acid 2-(2-prop-2-yn-1-yloxy) ethoxy)ethyl was added thereto in the form of a dehydrated tetrahydrofuran solution while washing down in 3 mL×twice thereby starting the reaction.

The reaction solution was stirred at room temperature for 1.5 hours, subsequently passed through a short column of silica gel (8 g) thereby terminating the reaction and eluted with 100 mL of ethyl acetate. The eluate was washed with 2 mL of a saturated aqueous solution of sodium chloride, 2 mL of water×twice and 2 mL of a saturated aqueous solution of sodium chloride, dried over sodium sulfate and subsequently concentrated under reduced pressure thereby obtaining 756.9 mg of a brownish oily substance. The oily substance was subjected to silica gel column chromatography (65 g, 2.4 cm inner diameter×27 cm length) using hexane-ethyl acetate (4:6) as an eluent thereby obtaining 426.9 mg (0.7710 mmol; yield 71%) of the titled compound as a light yellow oily substance.
$^1$H-NMR (270 MHz, CDCl$_3$, TMS): δ (ppm) 0.58 (9H, s, t-Bu), 2.37 (3H, s, H-14'''), 3.57-3.67 (6H, m, H-4''', 5''' and 6'''), 4.10-4.13 (2H, m, H-7'''), 4.34 (2H, s, H-3'''), 4.47 (1H, brs, H-3), 6.85 (1H, s, H-1), 7.19-7.38 (6H, m, H-5", 6", 9''', 10''', 12''', 13'''), 7.72-7.75 (2H, m, H-2" and 4"), 7.98 (1H, s, H-3'), 8.44 (1H, brs, H-5')
high resolution MS: calcd for C$_{29}$H$_{35}$N$_3$Na$_1$O$_6$S$_1$ 576.21443; found 576.21478

Production Example 7

Synthesis of 1-(4-iodophenyl)-4,4-dimethyl-2-(1H-1,2,4-triazol-1-yl)pent-1-en-3-one

104.6 mg (0.625 mmol) of 3,3-dimethyl-1-(1H-1,2,4-triazol-1-yl)butan-2-one was dissolved in 1 mL of acetic anhydride. 87.4 mg (0.632 mmol) of potassium carbonate and 146.0 mg (0.629 mmol) of 4-iodobenzaldehyde were added thereto, and the resultant solution was heated to 100° C. thereby starting the reaction. Five hours later from starting the reaction, 3 mL of water was added thereto thereby terminating the reaction. 3 mL of water was further added thereto, and the resultant was extract with 16 mL of ethyl acetate. The resultant was washed twice with 1 mL of a saturated aqueous solution of sodium chloride, dried over sodium sulfate and subsequently concentrated under reduced pressure thereby obtaining 255.6 mg of a mixture of a light orange oily substance and a white solid. The mixture was subjected to silica gel column chromatography (19 g, 1.4 cm inner diameter×20 cm length) using hexane-ethyl acetate (8:2) as an eluent thereby obtaining 101.5 mg (0.2663 mmol; yield 43%) of the titled compound as a white solid.

Production Example 8

Synthesis of (E)-1-(4-iodophenyl)-4,4-dimethyl-2-(1H-1,2,4-triazol-1-yl)pent-1-en-3-one 84.0 mg (0.211 mmol) of the mixture of EZ forms of 1-(4-iodophenyl)-4,4-dimethyl-2-(1H-1,2,4-triazol-1-yl)pent-1-en-3-one obtained in Production Example 7 was dissolved in methanol and the resultant solution was irradiated with a UV lamp while cooling with ice. 1.5 hours later, the irradiation was halted and the resultant solution was concentrated under reduced pressure thereby obtaining 80.4 mg (0.2109 mmol) of a mixture of a colorless clear oily substance and a white solid containing mostly (E)-1-(4-iodophenyl)-4,4-dimethyl-2-(1H-1,2,4-triazol-1-yl)pent-1-en-3-one and barely (Z)-1-(4-iodophenyl)-4,4-dimethyl-2-(1H-1,2,4-triazol-1-yl)pent-1-en-3-one.

Z form

$^1$H-NMR (270 MHz, CD$_3$OD): δ (ppm) 0.99 (9H, s, t-Bu), 7.13 (1H, m, H-2" or 6"), 7.16 (1H, m, H-2" or 6"), 7.24 (1H, brs, H-1), 7.73 (1H, m, H-3" or 5"), 7.77 (1H, m, H-3" or 5"), 8.12 (1H, s, H-3'), 8.92 (1H, s, H-5')

E form $^1$H-NMR (270 MHz, CD$_3$OD): δ (ppm) 1.26 (9H, s, t-Bu), 6.62 (1H, m, H-2" or 6"), 6.66 (1H, m, H-2" or 6"), 7.64 (1H, m, H-3" or 5"), 7.68 (1H, m, H-3" or 5"), 7.73 (1H, brs, H-1), 8.23 (1H, s, H-3'), 8.45 (1H, s, H-5')

Production Example 9

Synthesis of (E)-1-(4-iodophenyl)-4,4-dimethyl-2-(1H-1,2,4-triazol-1-yl)pent-1-en-3-ol A mixture containing (E)-1-(4-iodophenyl)-4,4-dimethyl-2-(1H-1,2,4-triazol-1-yl)pent-1-en-3one as the main component was dissolved in 2 mL of methanol and 10.4 mg (0.274 mmol) of sodium borohydride was added thereto thereby starting the reaction. The reaction solution was stirred at room temperature for 1.5 hours, 5.1 mg (0.14 mmol) of sodium borohydride was added thereto, and 1 hour later therefrom 6.3 mg (0.17 mmol) of sodium borohydride was further added thereto. Three hours later from the reaction initiation, 3 mL of water was added thereby terminating the reaction, and the resultant was extracted three times with 18 mL of ethyl acetate. During extraction, 0.3 mL of 1 M hydrochloric acid was added due to poor separation. The resultant was washed twice with 1 mL of a saturated aqueous solution of sodium chloride, dried over sodium sulfate and subsequently concentrated under reduced pressure thereby obtaining 89.2 mg of a colorless clear oily substance. The oily substance was subjected to silica gel column chromatography (11 g, 1.2 cm inner diameter×16 cm length) using hexane-ethyl acetate (7:3) as an eluent thereby obtaining 61.4 mg (yield 73%) of the titled compound as a white solid.

$^1$H-NMR (270 MHz, CD$_3$OD): δ (ppm) 0.56 (9H, s, t-Bu), 4.54 (1H, s, H-3) 6.95 (1H, s, H-1), 7.09 (1H, m, H-2" or 6"), 7.12 (1H, m, H-2" or 6"), 7.68 (1H, m, H-3" or 5"), 7.70 (1H, m, H-3" or 5"), 7.99 (1H, s, H-3'), 8.82 (1H, s, H-5')

Production Example 10

Synthesis of 4-methylbenzene sulfonic acid (E)-2-(2-(3-(4-(3-hydroxy-4,4-dimethyl-2-(1H-1,2,4-triazol-1-yl)pent-1-en-1-yl)phenyl)prop-2-yn-1-yloxy) ethoxy)ethyl

31.2 mg (81.8 μmol) of (E)-1-(4-iodophenyl)-4,4-dimethyl-2-(1H-1,2,4-triazol-1-yl)pent-1-en-3-ol was dissolved in 0.5 mL of dehydrated tetrahydrofuran under an argon stream, and 22 μL (158 μmol) of triethylamine, 2.4 mg (13 μmol) of copper(I) iodide and 1.6 mg (2.3 μmol) of trans-dichlorobis(tripherrylphosphine)palladium (II) were sequentially added thereto. After stirring at room temperature for 30 minutes, 38.1 mg (127 μmol) of 4-methylbenzene sulfonic acid 2-(2-prop-2-yn-1-yloxy)ethoxy)ethyl was added thereto in the form of a dehydrated tetrahydrofuran solution while washing down in 0.1 mL×twice. The reaction solution was stirred at room temperature for 1.5 hours, subsequently passed through a short column of silica gel (0.5 g) thereby terminating the reaction and extracted with 25 mL of ethyl acetate. The eluate was washed with 2 mL of water and 1 mL of a saturated aqueous solution of sodium chloride, dried over sodium sulfate and subsequently concentrated under reduced pressure thereby obtaining 69.7 mg of an orange oily substance. The oily substance was subjected to silica gel column chromatography (10 g, 1.2 cm inner diameter×18 cm length) using hexane-ethyl acetate (3:7) as an eluent thereby obtaining 37.8 mg (68.3 mmol; yield 84%) of the titled compound as a light yellow oily substance.

$^1$H-NMR (270 MHz, CDCl$_3$, TMS): δ (ppm) 0.66 (9H, s, t-Bu), 2.44 (3H, s, H-14'''), 3.64-3.74 (6H, m, H-4''', 5''' and 6'''), 4.19 (2H, t, J=4.6 Hz, H-7'''), 4.41 (2H, s, H-3'''), 4.58 (1H, brs, H-3), 6.93 (1H, s, H-1), 7.34 (4H, m, H-2'', 6'', 10''' and 12'''), 7.49 (2H, m, H-3'' and 5'), 7.81 (2H, m, H-9''' and 13'''), 8.06 (1H, brs, H-3'), 8.49 (1H, brs, H-5')

high resolution MS: calcd for C$_{29}$H$_{35}$N$_3$Na$_1$O$_6$S$_1$ 576.21443; found 576.21416

Example 1

Synthesis of (E)-1-(3-(2,5,8,11-tetraoxatetradec-13-yn-14-yl)phenyl)-4,4-dimethyl-2-(1H-1,2,4-triazol-1-yl)pent-1-en-3-ol 323.5 mg (8.088 mmol) of 60% sodium hydride was added to 3 mL of 2-methoxyethanol under an argon stream and the resultant solution was stirred at room temperature for 15 minutes. 395.7 mg (0.7146 mmol) of 4-methylbenzene sulfonic acid (E)-2-(2-(3-(3-(3-hydroxy-4,4-dimethyl-2-(1H-1,2,4-triazol-1-yl)pent-1-en-1-yl)phenyl)prop-2-yn-1-yloxy)ethoxy)ethyl was added thereto while washing down with 3 mL of 2-methoxyethanol×three times thereby starting the reaction. After stirring at room temperature for 30 minutes, the reaction solution was heated to 80° C. and stirred for 1 bout; to which 20 mL of a saturated aqueous solution of ammonium chloride was added while cooling with ice, thereby terminating the reaction. 20 mL of water was added thereto, and the resultant was extracted three times with 60 mL of ethyl acetate. The resultant was washed twice with 3 mL of a saturated aqueous solution of sodium chloride, dried over sodium sulfate and subsequently concentrated under reduced pressure thereby obtaining 432.9 mg of a mixture of a brownish oily substance and a colorless clear oily substance. The mixture was subjected to silica gel column chromatography (43 g, 2.4 cm inner diameter ×18.5 cm length) using hexane-ethyl acetate (9:1-0:10 step gradient) as an eluent to remove impurities and subsequently eluted with an eluent of ethyl acetate-methanol (99:1) thereby obtaining 271.6 mg of a mixture of the titled compound and impurities. The mixture was separated by HPLC (column, YMC-Pack Hydrosphere C 18 (20 mm inner diameter×150 mm length); flow rate 8 mL/min; detection UV254 nm) using 70% methanol/water as an eluent thereby obtaining 248.4 mg (0.5428 mmol; yield 76%) of the titled compound as a colorless clear oily substance. (total yield 22%)

$^1$H-NMR (270 MHz, CDCl$_3$, TMS): δ (ppm) 0.66 (9H, s, t-Bu), 3.38 (3H, s, H-10'''), 3.49-3.80 (12H, m, H-4''', 5''', 6''', 7''', 8''' and 9'''), 4.26 (1H, d, J=8.9 Hz, OH), 4.44 (2H, s, H-3'''), 4.54 (1H, d, J=8.9 Hz, H-3), 6.92 (1H, s, H-1), 7.31-7.45 (4H, m, H-2'', 3'', 4'' and 6''), 8.05 (1H, s, H-3'), 8.50 (1H, s, H-5')

UV ξmax (MeOH) nm (ε): 241 (33000)

high resolution MS: calcd for C$_{25}$H$_{35}$N$_3$Na$_1$O$_5$ 480.24744; found 480.24698

The titled compound was optically resolved by chiral HPLC (column, CHIRAL CEL OD-H (10 mm inner diameter×250 mm length); 18% 2-propanol/hexane; flow rate 4.5 ml/min; detection UV254 nm). The compounds eluted first were the (−) form and the compounds eluted latter were the (+) form.

(−) form
ee>99.96(%)
[α]$^{29}_D$−2.8 (MeOH; c0.52)
(+) form
ee=99.96(%)
[α]$^{30}_D$+3.6(MeOH; c0.54)

Example 2

Synthesis of (E)-1-(3-(3-(2-(2-butoxyethoxy)ethoxy) prop-1-yn-1-yl)phenyl)-4,4-dimethyl-2-(1H-1,2,4-tri azol-1-yl)pent-1-en-3-ol The reaction was carried out by the same method as described in Example 1 using 1-butanol in place of 2-methoxyethanol thereby obtaining the titled compound (total yield 26%).

$^1$H-NMR (270 MHz, CDCl$_3$, TMS): δ (ppm) 0.66 (9H, s, t-Bu), 0.91 (3H, t, J=7.3 Hz, H-11'''), 1.22-1.43 (2H, m, H-10'''), 1.52-1.62 (2H, m, H-9'''), 3.47 (2H, t, J=6.6 Hz, H-8'''), 3.59-3.81 (8H, m, H-4''', 5''', 6''' and 7'''), 4.27 (1H, d, J=8.6 Hz, OH), 4.45 (2H, s, H-3'''), 4.55 (1H, d, J=8.6 Hz, H-3), 6.92 (1H, s, H-1), 7.31-7.45 (4H, m, H-2'', 3'', 4'' and 6''), 8.05 (1H, s, H-3'), 8.50 (1H, s, H-5')

UV λmax (MeOH) nm (ε): 241 (35000)

high resolution MS: calcd for C$_{26}$H$_{37}$N$_3$Na$_1$O$_4$ 478.26818; found 478.26751

The titled compound was optically resolved by chiral HPLC (column, CHIRAL CEL OD-H (10 mm inner diameter×250 mm length); 10% 2-propanol/hexane; flow rate 4.5 mL/min; detection UV254 nm). The compounds eluted first were the (−) form and the compounds eluted latter were the (+) form.

(−) form
ee>99.96(%)
[α]$^{32}_D$−4.4 (MeOH; c0.5)
(+) form
ee=99.96(%)
[α]$^{32}_D$+3.8 (MeOH; c0.5)

Example 3

Synthesis of (E)-1-(4-(2,5,8,11-tetraoxatetradec-13-yn-14-yl)phenyl)-4,4-dimethyl-2-(1H-1,2,4-triazol-1-yl)pent-1-en-3-ol

75.6 mg (1.89 mmol) of 60% sodium hydride was added to 2 mL of 2-methoxyethanol under an argon stream, and the resultant solution was stirred at room temperature for 20 minutes. 87.2 mg (0.158 mmol) of 4-methylbenzene sulfonic acid (E)-2-(2-(3-(4-(3-hydroxy-4,4-dimethyl-2-(1H-1,2,4-triazol-1-yl)pent-1-en-1-yl)phenyl)prop -2-yn-1-yloxy) ethoxy)ethyl was added thereto while washing down with 1 mL of 2-methoxyethanol×three times and the resultant solution was heated to 60° C. thereby starting the reaction. After stilling for 7.5 hours, 10 mL of a saturated aqueous solution of ammonium chloride was added thereto thereby terminating the reaction. 10 mL of water was added, and the resultant was extracted three times with 30 mL of ethyl acetate. The resultant was washed twice with 2 mL of a saturated aqueous solution of sodium chloride, dried over sodium sulfate and subsequently concentrated under reduced pressure thereby obtaining 97.7 mg of a yellow oily substance. The oily substance was subjected to silica gel column chromatography (10 g, 1.4 cm inner diameter×17 cm length) using dichloromethane-methanol (19:1) as an eluent thereby obtaining 61.0 mg (0.134 mmol; yield 85%) of the titled compound as a light yellow oily substance. (Total yield 16%) The oily substance was purified by HPLC (column, YMC-Pack Hydrosphere C18 (20 mm inner diameter×150 mm length); flow rate 8 mL/min; detection UV254 nm) using 65% methanol/water as an eluent thereby obtaining a colorless clear oily substance.

$^1$H-NMR (270 MHz, CDCl$_3$, TMS): δ (ppm) 0.66 (9H, s, t-Bu), 3.38 (3H, s, H-10'''), 3.54-3.80 (12H, m, H-4''', 5''', 6''', 7''', 8''' and 9'''), 4.27 (H1, d, J=8.9 Hz, OH), 4.45 (2H, s, H-3'''), 4.57 (1H, d, J=8.9 Hz, H-3), 6.93 (1H, s, H-1), 7.32-7.35 (2H, m, H-2'' and 6''), 7.47-7.50 (2H, m, H-3'' and 5''), 8.05 (1H, s, H-3'), 8.48 (1H, s, H-5')
UV λmax (MeOH)nm (ε): 270 (24000)
high resolution MS: calcd. for C$_{25}$H$_{35}$N$_3$Na$_1$O$_5$ 480.24744; found 480.24734

The titled compound was optically resolved by chiral HPLC (column, CHIRAL CEL OD-H (10 mm inner diameter×250 mm length); 15% 2-propanol/hexane; flow rate 4.5 mL/min; detection UV254 nm) thereby obtaining the (−) form and the (+) form. The compounds eluted first were the (−) form and the compound eluted latter were the (+) form.
(−) form
ee>99.84(%)
$[α]^{32}{_D}$−35 (MeOH; c0.81)
(+) form
ee=99.84(%)
$[α]^{32}{_D}$+36 (Me0H; c0.82)

Example 4

Synthesis of (E)-1-(3-(3-(2-(2-butoxyethoxy)ethoxy) prop-1-yn-1-yl)phenyl)-4,4-dimethyl-2-(1H-1,2,4-triazol-1-yl) pent-1-en-3-ol

The reaction was carried out by the same method as described in Example 3 using 1-butanol in place of 2-methoxyethanol thereby obtaining the titled compound (total yield 15%).

$^1$H-NMR (500 MHz, CD$_3$OD): δ (ppm) 0.22 (9H, s, t-Bu), 0.48 (3H, t, J=7.6 Hz, H-11'''), 0.90-0.98 (2H, m, H-10'''), 1.08-1.14 (2H, m, H-9'''), 3.04 (2H, t, J=6.7 Hz, H-8'''), 3.14-3.16 (2H, m, H-7'''), 3.20-3.22 (2H, m, H-6'''), 3.25-3.26 (2H, m, H-5'''), 3.31-3.33 (2H, m, H-4'''), 4.00 (2H, s, H-3'''), 4.24 (1H, s, H-3), 6.66 (1H, s, H-1), 6.97-6.98 (2H, m, H-2'' and 6''), 7.05-7.06 (2H, m, H-3'' and 5''), 7.65 (1H, s, H-3'), 8.48 (1H, s, 1H, s, H-5')
UV λmax (MeOH) nm (ε): 271 (24000)
high resolution MS: calcd for CH$_{26}$H$_{37}$N$_3$Na$_1$O$_4$ 478.26818; found 478.26763

The titled compound was optically resolved by chiral HPLC (column, CHIRAL CEL OD-H (10 mm inner diameter×250 mm length); 8% 2-propanol/hexane; flow rate 4.5 mL/min; detection UV254 nm) thereby obtaining the (−) form and the (+) form. The compounds eluted first were the (−) form and the compounds eluted latter were the (+) form.
(−) form
ee>99.9(%)
$[α]^{27}{_D}$−36 (MeOH; c0.78)
(+) form
ee>99.9(%)
$[α]^{28}{_D}$+32 (MeOH; c0.75)

Example 5

Synthesis of (−)-(S)-(E)-1-(3-(2,5,8,11-tetraoxatetradec-13-yn-14-yl)phenyl)-4,4-dimethyl-2-(1H-1,2,4-triazol-1-yl)pent-1-en-3-ol 57.0 mg (0.12 mmol) of (E)-1-(3-(2,5,8,11-tetraoxatetradec-13-yn-14-yl)phenyl)-4,4-dimethyl-2-(1H-1,2,4-triazol-1-yl)pent-1-en-3-ol was dissolved in 5 mL of toluene under an argon stream. 420.8 mg (1.25 mmol) of N-(para-toluenesulfonyl)-L-phenylalanylchloride was added thereto, and the resultant solution was stirred at 130° C. for 3 hours. After the temperature of the solution was back to room temperature, 12 mL of an aqueous solution of saturated sodium hydrogen carbonate was added thereto, and the resultant was extracted three times with 15 mL of ethyl acetate. The organic layer was washed three times with a saturated aqueous solution of sodium chloride, dried over sodium sulfate and subsequently concentrated under reduced pressure thereby obtaining 117 mg of a viscous yellow oily substance. The oily substance was subjected to silica gel column chromatography (14 g, 15 mm inner diameter×140 mm length) using hexane-ethyl acetate (0-100%, step gradient) as an eluent thereby obtaining 12.8 mg (28 nmol, yield 22%, e.e 98.4%) of the titled compound.

$^1$H-NMR (270 MHz, CDCl$_3$, TMS): δ (ppm) 0.52 (9H, s), 2.23 (3H, s), 2.89 (1H, dd), 3.10 (1H, dd, J=13.8 and 6.9 Hz), 3.34 (3H, s), 3.49-3.84 (12H, m), 4.36 (1H, dd, J=7.9 and 7.3 Hz), 4.46 (2H, s), 5.82 (1H, s), 7.08-7.63 (14H, m), 8.14 (1H, s), 8.80 (1H, s)

Example 6

Synthesis of (−)-(S)-(E)-1-(3-(2,5,8,11-tetraoxatetradec-13-yn-14-yl)phenyl)-4,4-dimethyl-2-(1H-1,2,4-triazol-1-yl)pent-1-en-3-ol 50.3 mg (0.11 mmol) of (E)-1-(3-(2,5,8,11-tetraoxatetradec-13-yn-14-yl)phenyl)-4,4-dimethyl-2-(1H-1,2,4-triazol-1-yl)pent-1-en-3-ol was dissolved in 5 mL of toluene under an argon stream. 743.8 mg (2.20 mmol) of N-(para-toluenesulfonyl)-L-phenylalanylchloride was added thereto, and the resultant solution was stirred at 130° C. for 3 hours. After the temperature of the solution was back to room temperature, 10 mL of an aqueous solution of saturated sodium hydrogen carbonate was added thereto, and the resultant was extracted three times with 15 mL of ethyl acetate. The organic layer was washed three times with a saturated aqueous solution of sodium chloride, dried over sodium sulfate and subsequently concentrated under reduced pressure thereby obtaining 251 mg of a viscous yellow oily substance. The oily substance was subjected to silica gel column chromatography (11 g, 14 mm inner diameter×150 mm length) using hexane-ethyl acetate (0-100%, step gradient) as an eluent and further subjected to ODS HPLC (YMC-Pack ODS-AQ (20 mm inner diameter×150 mm length), 80%MeOH, 8.0 mL/min, 254 nm) thereby obtaining 32.2 mg (0.027 mmol) of an ester of the titled compound. 20.2 mg of the obtained substance was dissolved in 1.5 mL of tetrahydrofuran, and 1.5 mL of an aqueous solution of 5 M sodium hydroxide was added thereto, followed by stirring the resultant at 60° C. for 6 hours. The temperature of the solution was back to room temperature and the solution was extracted three times with 12 mL of ethyl acetate. The organic layer was washed three times with a saturated aqueous solution of sodium chloride, dried over sodium sulfate and subsequently concentrated under reduced pressure thereby obtaining 14 mg of a colorless clear oily substance. The oily substance was subjected to silica gel column chromatography (10 g, 15 mm inner diameter×135 mm length) using hexane-ethyl acetate (0-100%, step gradient) as an eluent thereby obtaining 11.5 mg (0.025 mmol, yield 36%) of the titled compound.

$^1$H NMR (270 MHz, CDCl$_3$, TMS): δ (ppm) 0.52 (9H, s), 2.23 (3H, s), 2.89 (1H, dd), 3.10 (1H, dd, J=13.8 and 6.9 Hz), 3.34 (3H, s), 3.49-3.84 (12H, m), 4.36 (1H, dd, J=7.9 and 7.3 Hz), 4.46 (2H, s), 5.82 (1H, s), 7.08-7.63 (14H, m), 8.14 (1H, s), 8.80 (1H, s)

Comparative Example 1

Synthesis of 1-(4-(4-((2-(2-butoxyethoxy)ethoxy)methyl)-1H-1,2,3-triazol-1-yl)phenyl)-4,4-dimethyl-2-(1H-1,2,4-triazol-1-yl)pent-1-en-3-ol The titled compound was synthesized in accordance with the method described in Non Patent Literature 1 to obtain the (+) form and the (−) form by the optical resolution.

Test Example 1

Thale Cress Seed Germination Inhibition Test (1)

Figure 1:
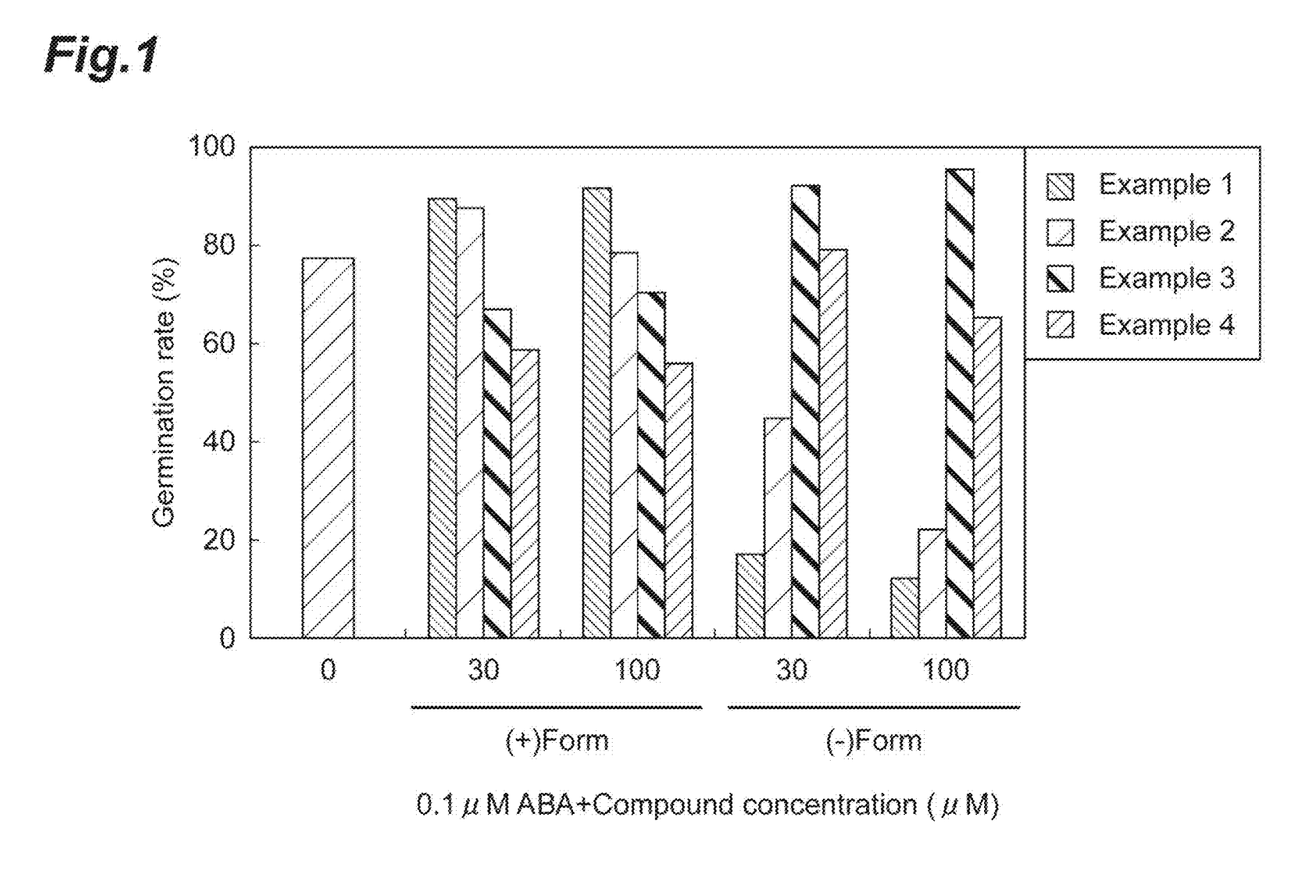
FIG. 1 is a graph showing the examination results of the influence of the compounds of Examples 1 to 4 on the seed germination of thale cress.
Figure 2:
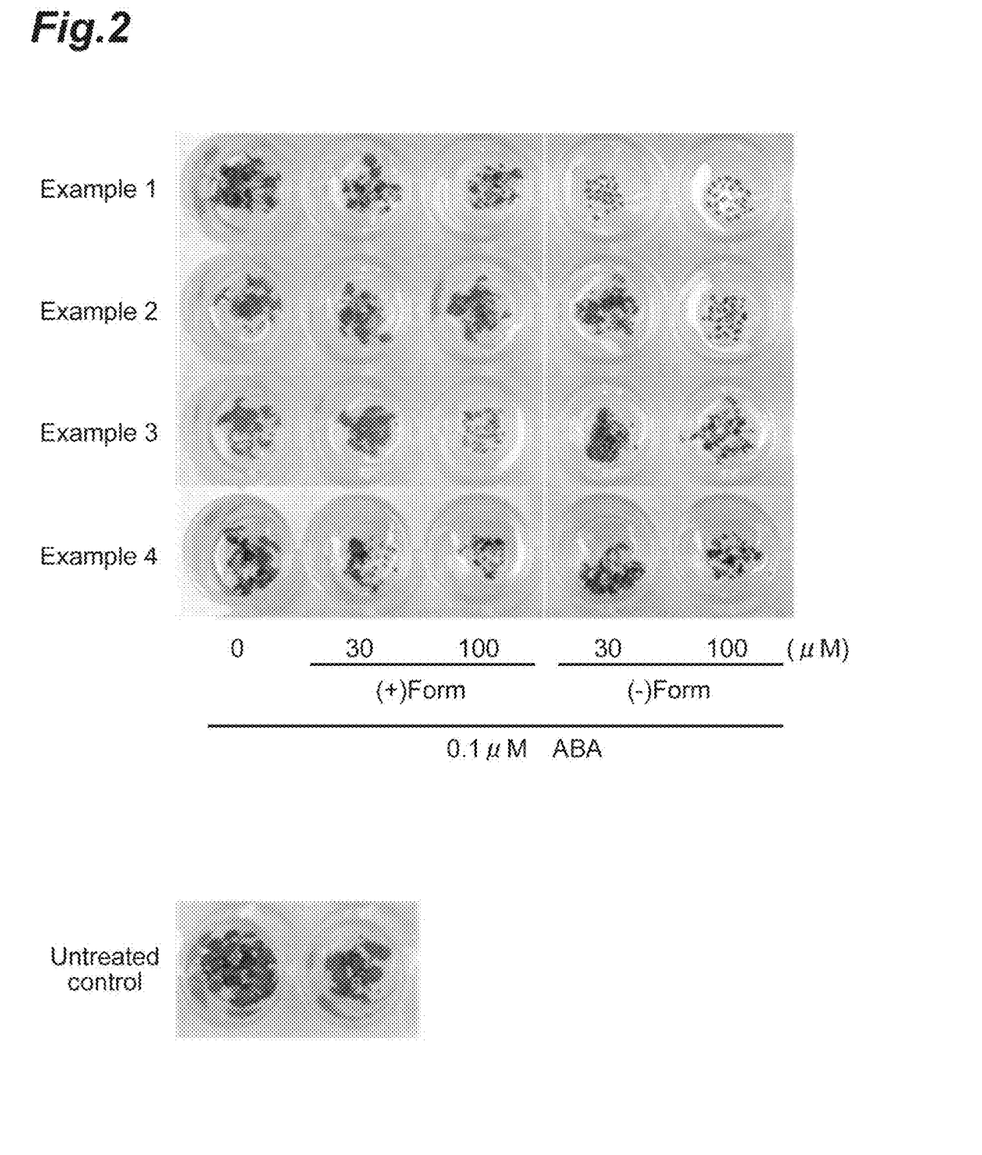
FIG. 2 includes photographs showing the examination results of the influence of the compounds of Examples 1 to 4 on the seed germination of thale cress.

Seeds of thale cress (*Arabidopsis thaliana*, Col-0) were immersed in 500 of an aqueous solution of 70% ethanol for 30 minutes, subsequently in 500 μL of 100% ethanol for 1 minute, washed three times in 1 mL of distilled water, then immersed in distilled water and, in a dark place, verbalized at 4° C. for 3 days. A solution of the sample in methanol and a solution of ABA in methanol were put in a 1.5 mL microtube, and methanol was removed therefrom under reduced pressure. An aqueous solution of 0.5% agar (containing 1/2 MS medium inorganic salts) at 70° C. was added thereto, followed by stirring the resultant. The obtained solution was placed in a 96-well plate to provide the medium containing the sample. 20 to 30 vernalized seeds of thale cress were planted in each well and cultured at 22° C. under continuous light to monitor the number of seeds germinated over time. The germination rate was calculated in accordance with the following formula (1). Note that the medium prepared using methanol in the same manner as above was used as an untreated control and a germination rate of 100% was achieved 72 hours later from the seed plantation. Germination rates 72 hours later from the seed plantation are shown in FIG. 1 and initial growth conditions of thale cress 120 hours later are shown in FIG. 2. It was revealed that the application of the compounds of Examples 1 to 4 inhibits the seed germination.

Germination rate (%)=Number of seeds germinated/Number of seeds planted×100 . . . (1)

Test Example 2

Thale Cress Seed Germination Inhibition Test (2)

Figure 3:
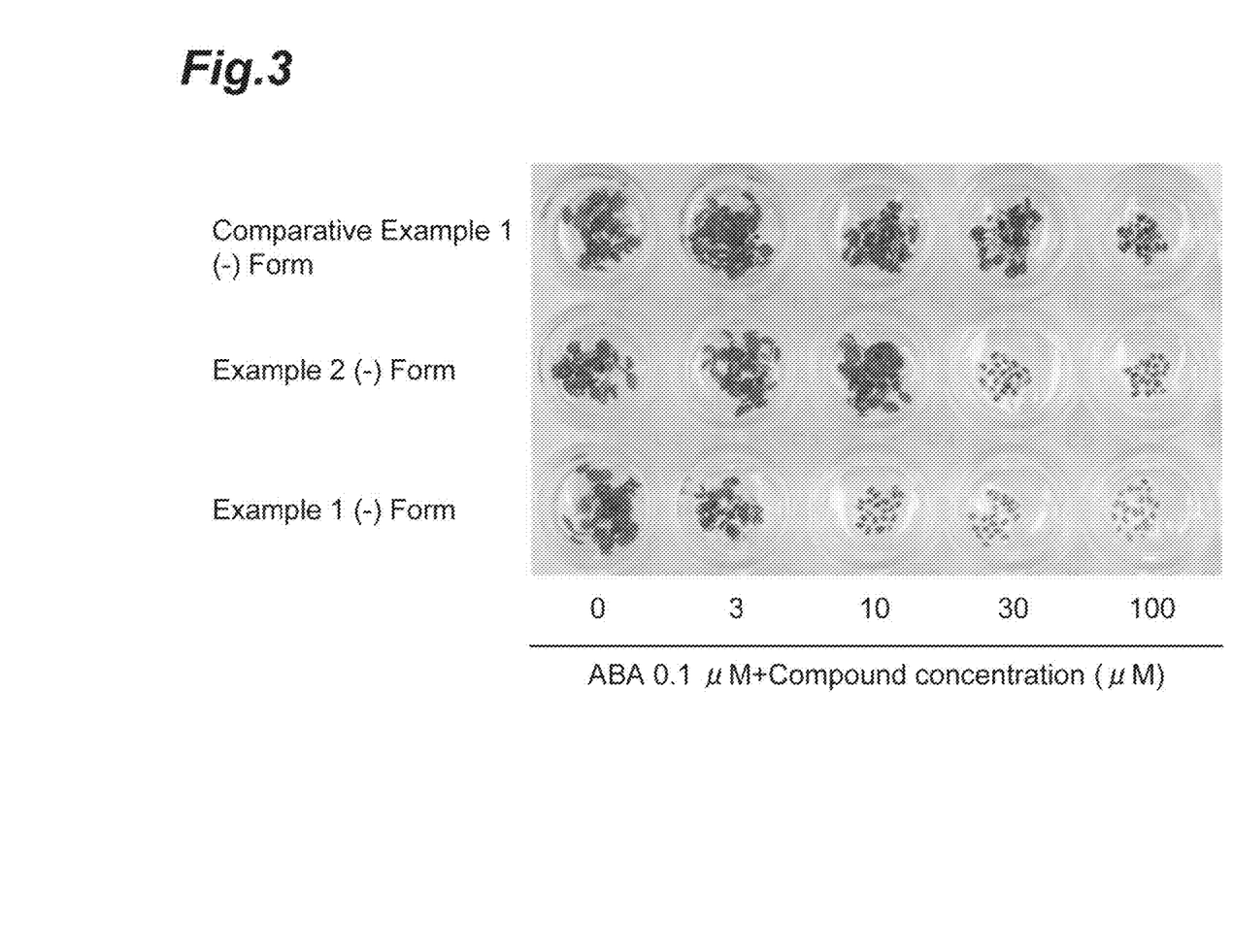
FIG. 3 is a photograph showing the examination results of the influence of the compounds of Examples 1 and 2 and the compound of Comparative Example 1 on the seed germination of thale cress.

The same test was carried out as in Test Example 1 using, as samples, the (−) form of Example 1, the (−) form of Example 2 and the (−) form of Comparative Example 1. Germination conditions 120 hours later from the seed plantation are shown in FIG. 3. It was revealed that, when compared with the (−) form of Comparative Example 1, the (−) form of Example 1 and the (−) form of Example 2 can inhibit the seed germination even in lower concentrations.

Test Example 3

Rice Plant Second Leaf Sheath Extension Inhibition Test

Figure 4:
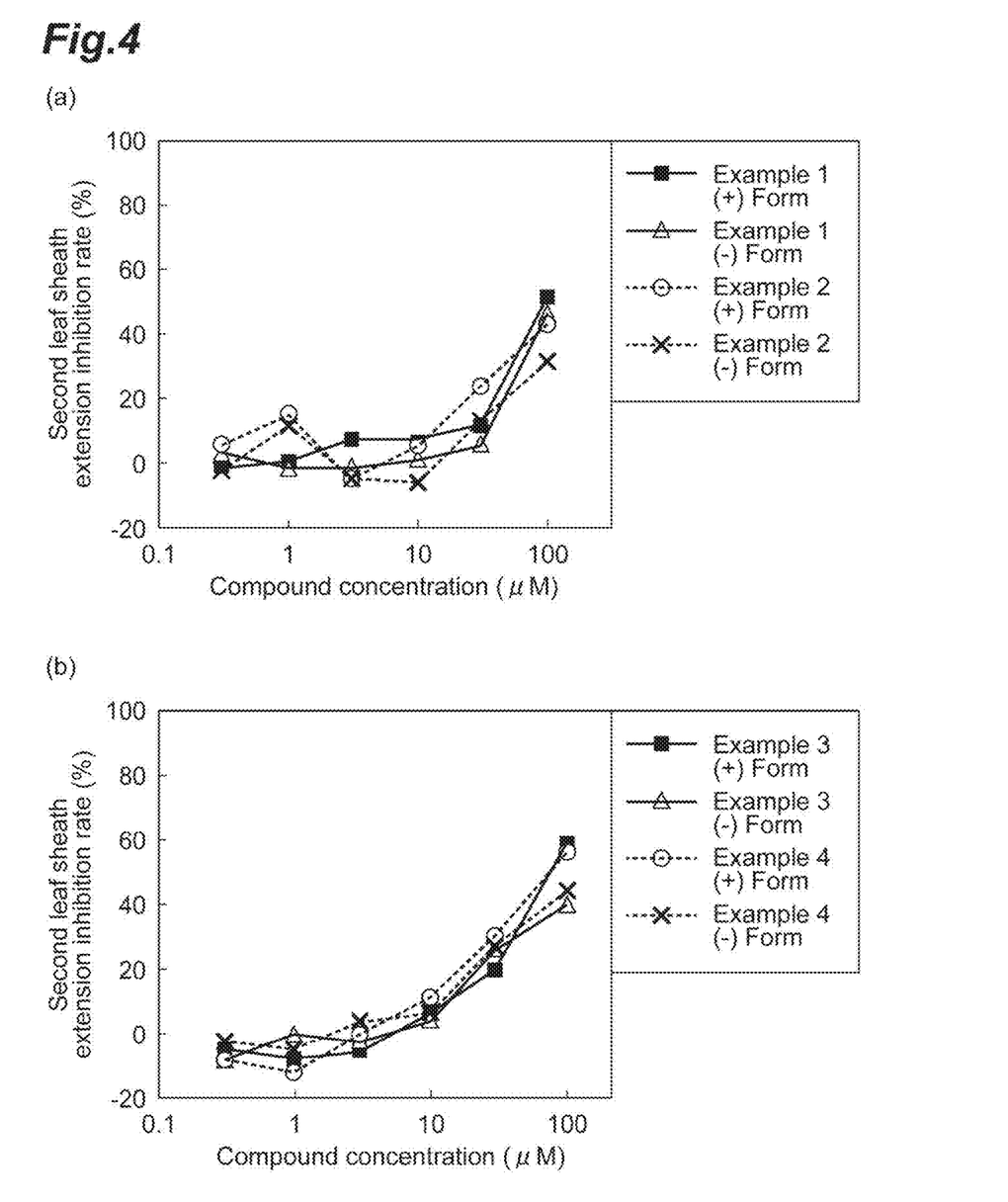
FIG. 4 includes graphs showing the examination results of the influence of the compounds of Examples 1 to 4 on the extension of the second leaf sheath of a rice plant.

Seeds of a rice plant (*Oryza saliva L. cv. Nihonbare*) were immersed in ethanol for 5 minutes, subsequently washed ten times in water, immersed in water and cultured at 30° C. under continuous light for 3 days for germination. A solution of the sample in methanol was put in a culture tube, and methanol was removed therefrom under reduced pressure, followed by adding 2 mL of deionized water thereto. Seven germinated seeds were placed in each tube, cultured with a cap on under continuous light at 30° C. for 7 days and subsequently measured for the length of the second leaf sheath, based on which the inhibition rate was calculated in accordance with the following formula (2). Note that those cultured only in deionized water were used as controls. The results are shown in FIG. 4. It was revealed that the high concentration application of the compounds of Examples 1 to 4 inhibits the leaf sheath extension.

Extension inhibition rate (%)={1-(Second leaf sheath length of each specimen/Second leaf sheath length of control)}×100 . . . (2)

Test Example 4

Abscisic acid 8'-hydroxylase CYP707A3 inhibition test

In a 1.5 mL microtube, 10 μL of a solution of substrate 250 μM ABA in potassium/phosphate buffer (KPB), 5 μL of a solution of the sample in dimethylformamide, 435 μL of KPB and 40 μL of abscisic acid 8'-hydroxylase CYP707A3+NADPH-P450 reductase ATR1 were put and heated at 30° C. for 10 minutes. 10 μL of a solution of 5 mg/mL NADPH in KPB was added thereto thereby starting the enzyme reaction. The reaction was carried out at 30° C. for 10 minutes at a rotation speed of 1000 rpm, and 25 μL of an aqueous solution of 1 M sodium hydroxide was added thereto thereby terminating the reaction. The reaction solution was allowed to stand at 4° C. for 30 minutes and subsequently 50 μL of 1 M hydrochloric acid was added thereto to convert the enzyme metabolite to phaseic acid (PA). The enzyme reaction solution was subjected to an OASIS HLB cartridge (1 cc, 30 mg; washed with 1 mL of methanol (1% acetic acid) and equilibrated with 1 mL of water (1% acetic acid)) and washed with 1 mL of 10% methanol/water (1% acetic acid) thereby eluting phaseic acid with 1 mL of methanol (1% acetic acid). The eluate was concentrated under reduced pressure (toluene was added to azeotrope acetic acid), the obtained substance was dissolved in 50 μL of methanol. 20 μL of the solution was subjected to HPLC (column, YMC-Pack Hydrosphere C18 (6 mm inner diameter×150 mm length); flow rate 1 mL/min; detection 254 nm) analysis. The CYP707A3 inhibition rate of the samples was calculated in accordance with the following formula (3). Note that dimethylformamide was used for the control in place of the sample solution. Each sample was tested with two different concentrations to calculate the 50% inhibition concentration (IC$_{50}$) based on the enzyme inhibition rates thereof The results are shown in Table 1.

Enzyme inhibition rate (%)={1-(PA peak area of each sample/PA peak area of control)}×100 . . . (3)

TABLE 1

| Sample | | IC$_{50}$ (nM) |
|---|---|---|
| Example 1 | (+) Form | 1200 |
| | (−) Form | 64 |
| Example 2 | (+) Form | 240 |
| | (−) Form | 12 |
| Example 3 | (+) Form | 7700 |
| | (−) Form | 1500 |
| Example 4 | (+) Form | 1000 |
| | (−) Form | 200 |
| Comparative Example 1 | (+) Form | 1100 |
| | (−) Form | 54 |

Test Example 5

Ent-kaurene oxidase CYP701A6 inhibition test

To a 1.5 mL microtube, 8 μL of an aqueous solution of 500 μM ent-kaurene as a substrate in 45% cyclodextrin and 8μL of a solution of the sample in dimethylformamide were put. 10 μL of 2.32 μM ent-kaurene oxidase CYP701A6 and 10 μL of 4.6 unit/mL NADPH-P450 reductase ATR2, heated at 30° C. for 5 minutes in advance, were added thereto. 304 μL of ultra-pure water, 40 μL of 500 mM KPB and 20 μL of an aqueous solution of 20 mM NADPH, heated at 30° C. for 10 minutes in advance, were added thereto thereby starting the enzyme reaction. The reaction was carried out at 30° C. for 30 minutes at a rotation speed of 1000 rpm and 100 μL of 1 M hydrochloric acid was added thereto thereby terminating the reaction. 5 μL of 10 μM abietic acid as the internal standard was added thereto, and the solution was extracted with 400 μL of ethyl acetate. The resultant was dried over sodium sulfate and subsequently concentrated under reduced pressure. 50 μL of methanol and 5 μL of 2 M trimethyl silyldiazomethane were added thereto to methylate carboxylic acid and the resultant was thy-solidified using nitrogen. The solidified product was dissolved in 150 μL of hexane and 1 μL of the resultant solution was subjected to a GC-MS analysis to detect the enzyme metabolite ent-kaurene acid. The CYP701A6 inhibition rate of the samples was calculated in accordance with the following formula (4). Note that the peak area of ent-kaurene acid was calculated from the peak area of m/z 273 and that ent-kaurene acid was identified from the area ratio of m/z 257, 213. The peak area of abietic acid was calculated from the area of m/z 256, and abietic acid was identified from the area ratio of m/z 316. Note that dimethylformamide was used for the control in place of the sample solution. Each sample was tested with two different concentrations to act late the 50% inhibition concentration (IC$_{50}$) based on the enzyme inhibition rates thereof. The results are shown in Table 2.

Enzyme inhibition rate (%)={1-(Ent-kaurene acid peak area of each sample/Abietic acid peak area of each sample/ (Ent-kaurene acid peak area of control/Abietic acid peak area of control }×100 . . . (4)

TABLE 2

| Sample | | IC$_{50}$ (nM) |
|---|---|---|
| Example 1 | (+) Form | 1600 |
| | (−) Form | 780 |
| Example 2 | (+) Form | 120 |
| | (−) Form | 62 |
| Example 3 | (+) Form | 17000 |
| | (−) Form | 8600 |
| Example 4 | (+) Form | 1500 |
| | (−) Form | 770 |
| Comparative Example 1 | (+) Form | 1300 |
| | (−) Form | 1200 |

Test Example 6

Thale Cress Growth Test

Five plant bodies of 2-week old thale cress (*Arabidopsis thaliaria*, Col-0) grown in Gelzan medium (containing MS medium mixed salts and 1% sucrose) were transplanted to a 200 mL-plastic pot containing a culture soil obtained by mixing vermiculite and premix in 1:1 and grown at 22° C. for 2 weeks under the condition of 16 hour light period—8 hour dark period. At this stage, the moisture content was adjusted so that the mass of the pot containing the plant and the culture soil was to be about 150 g. 50 ml, of a 50 μM aqueous solution of the (−) form of Example 1 (containing 0.05% Tween-20 and 0.2% MeOH) was sprayed to the above-ground part on 27 pots (135 seedlings of thale cress in total) once a day for 3 days. The pots on which above-ground part were sprayed with 50 mL of an aqueous solution free from the above compound (containing 0.05% Tween-20 and 0.2% MeOH) once a day for 3 days were used as controls. The pots were dry-treated for 12 days and subsequently watered, and the number of plant bodies survived 3 days later was counted, from which the survival rate was calculated in accordance with the following formula (5). The control pots had a thale cress survival rate of 15% after dry treatment, whereas the pots sprayed with the aqueous solution of the 50 μM (=) four of Example 1 had a thale cress survival rate of 75% after dry treatment. It was revealed that the withering due to dryness is reduced when the (−) form of the compound of Example 1 was sprayed to thale cress.

Survival rate (%)=Number of plant bodies survived (piece)/Total number of plant bodies (piece)×100 . . .(5)

The invention claimed is:
1. A compound represented by formula (I) or a salt thereof:

wherein R is a C1-6 alkyl group, and the C1-6 alkyl group optionally has a substituent selected from the group consisting of a halogen atom and a C1-6 alkoxy group.

2. The compound or the salt thereof according to claim 1, wherein R is an n-butyl group or a 2-methoxyethyl group.

3. An inhibitor of abscisic acid 8'-hydroxylase CYP707A, comprising the compound or the salt thereof according to claim 1.

4. A plant growth regulator comprising the compound or the salt thereof according to claim 1.

5. An inhibitor of abscisic acid 8'-hydroxylase CYP707A, comprising the compound or the salt thereof according to claim 2.

6. A plant growth regulator comprising the compound or the salt thereof according to claim 2.

* * * * *